US 6,811,994 B1

(12) United States Patent
Miyauchi et al.

(10) Patent No.: US 6,811,994 B1
(45) Date of Patent: Nov. 2, 2004

(54) METHOD FOR QUANTITATING TRIGLYCERIDES IN LIPOPROTEINS

(75) Inventors: Kazuhito Miyauchi, Nagaizumi-cho (JP); Shizuyo Takada, Nagaizumi-cho (JP); Tomomi Murakami, Nagaizumi-cho (JP); Akira Miike, Nagaizumi-cho (JP)

(73) Assignee: Kyowa Medex Co., Ltd., Tokyo (JP)

( * ) Notice: Subject to any disclaimer, the term of this patent is extended or adjusted under 35 U.S.C. 154(b) by 0 days.

(21) Appl. No.: 09/889,742

(22) PCT Filed: Jan. 20, 2000

(86) PCT No.: PCT/JP00/00246

§ 371 (c)(1),
(2), (4) Date: Jul. 20, 2001

(87) PCT Pub. No.: WO00/43537

PCT Pub. Date: Jul. 27, 2000

(30) Foreign Application Priority Data

Jan. 20, 1999 (JP) .......................... 11-012434

(51) Int. Cl.[7] .............................. C12Q 1/34; C12Q 1/28
(52) U.S. Cl. ................................. 435/18; 435/28
(58) Field of Search ................................... 435/18, 28

(56) References Cited

U.S. PATENT DOCUMENTS 4,215,993 A * 8/1980 Sanders ........................ 23/230

FOREIGN PATENT DOCUMENTS

| EP | 76211 | * 4/1983 |
| JP | 58-47499 | 3/1958 |
| JP | 57-137858 | 8/1982 |
| JP | 59-11197 | 1/1984 |
| JP | 8-201393 | 8/1996 |
| JP | 9121895 | 5/1997 |

OTHER PUBLICATIONS

Yoshida et al., "An influence of the free glycerol on triglyceride measurement, and the triglyceride measurement by free glycerol elimination method", Nissei Byoin Igaku Zasshi 12 (1): 53–7 (1984).*
Merck Index Eleventh Edition, entry 6681 (1989).*
Ohkubo et al., "Evaluation of a reagent for the determination of triglycerides without overdetermination of free glycerol", Rinsho Kensa 27 (3) : 329–32 (1983).*
Taku Yamamura, et al., *Apoliprotein E and Atherosclerosis*, Arteriosclerosis, vol. 25, Nos. 11, 12 (1998), pp. 415–419.
Taku Yamamura, et al., *Familial Type III Hyperlipoproteinemia*, Journal of Clinical and Experiemtnal Medicine, vol. 172, NO. 5 (1995), pp. 276–280.
Yoshiyatlata, *Triglycerides and Atherosclerosis*, Journal of Clinical and Experimental Medicine, vol. 164, No. 12 (1993), pp. 833–836.
Tamie Ando, *Monoclonal Antibody: Introduction of Experimental Procedure*, Kodansha Scientific (1991), p. 21.
Toshio Kajiuchi et al., *Stability and Partition of Modified Cellulase in Water–Benzyme, Toluene Sytem*, Journal of Chemical Engineering of Japan, vol. 20, No. 3 (1994), pp. 459–462.

* cited by examiner

*Primary Examiner*—Sandra E. Saucier
(74) *Attorney, Agent, or Firm*—Fitzpatrick, Cella, Harper & Scinto

(57) ABSTRACT

The present invention relates to a method for conveniently quantitating TGs contained in various lipoproteins. A method for quantitating trigyceride (TG) in a particular lipoprotein which comprises eliminating free glycerol from a sample containing free glycerol and TG in the particular lipoprotein, then allowing the resulting sample to react with lipoprotein lipase and an enzyme system which generates hydrogen peroxide from free glycerol, and quantitating the generated hydrogen peroxide, is provided.

24 Claims, 3 Drawing Sheets

METHOD FOR QUANTITATING TRIGLYCERIDES IN LIPOPROTEINS

TECHNICAL FIELD

The present invention relates to a method for quantitating triglycerides (TG) in lipids, which are significant in a field of clinical laboratory test, particularly, as a risk factor of arteriosclerosis.

BACKGROUND ART

At present, in a field of clinical laboratory test, cholesterol in high density lipoprotein (HDL) is frequently determined as a risk factor, i.e., negative factor, of arteriosclerosis, while cholesterol in low density lipoprotein (LDL) is also determined as a positive factor. On the other hand, it has been elucidated by many epidemiological searches that hyperlipemia is a primary factor in development of an arteriosclerotic disease which is accompanied by an ischemic heart disease as a major symptom. In addition, among apoproteins E of very low density lipoproteins (VLDL), E1 is incorporated in the receptor, but E2 relating to III type hyperlipemia is not [Arteriosclerosis, 25 (11/12), 415–420 (1998); Journal of Clinical and Experimental Medicine, 172 (5), 276–280 (1995)]. Thus, the lipoproteins have so far been mentioned as a risk factor of arteriosclerosis in various aspects.

In recent years, it has been said that the difference in the kind and quantity of lipids contained in lipoproteins is involved in various diseases. Among them, it has also been reported that LDL, particularly, small dense LDL is a positive factor for closely related arteriosclerosis in a familial hyperlipemia. Small dense LDL is produced from VLDL by action of a TG catabolic enzyme. The ratio of the TG content to the cholesterol content has been altered in the small dense LDL in comparison with normal LDL, and the TG content is increased [Journal of Clinical and Experimental Medicine, 164 (12), 833–836 (1993)]. It has been considered, accordingly, that high TG concentration in LDL (an index of small dense LDL) enhances the risk of arteriosclerosis.

As for a method for specifically quantitating TG in each lipoprotein, for example, a colorimetry or other such method can be considered. In the colorimetry, each lipoprotein is fractionated by ultracentrifugation, and then TG contained in the fraction is treated, for example, with an enzyme system comprising lipoprotein lipase (LPL), glycerol kinase (GK) and glycerol-3-phosphate oxidase to generate hydrogen peroxide, with which a chromogen is developed together with a peroxidase (POD). This method, however, is very troublesome because it requires a great deal of time and effort for ultracentrifugation.

DISCLOSURE OF THE INVENTION

The purpose of the present invention is to provide a method for conveniently quantitating triglycerides (TGs) contained in various lipoproteins.

In serum or plasma samples, there are free glycerol and TG in various lipoproteins. In the invention, TG contained in a particular lipoprotein among these diverse lipoproteins is intended to be specifically quantitated without isolation of the aimed lipoprotein. For this purpose, free glycerol having an influence on the quantitation have to be converted into some inert form somehow, as well as TGs contained in lipoproteins other than the particular one have to be altered in advance or inhibited so that they cannot be involved in the reaction.

The present invention relates to a method for quantitating TGs in a particular lipoprotein which comprises eliminating free glycerol from a sample containing free glycerol and TG in the particular lipoprotein, then allowing the resulting sample to react with lipoprotein lipase (LPL) and an enzyme system which generates hydrogen peroxide from glycerol produced in said reaction, and quantitating the generated hydrogen peroxide.

As for samples containing TGs in lipoproteins, test specimens such as serum, plasma, and the like are exemplified. LPL means an enzyme (EC.3.1.1.34) which has a function decomposing TGs in lipoproteins into glycerol and fatty acids.

The enzyme system which generates hydrogen peroxide from glycerol includes a system containing glycerol kinase (GK) (EC.2.7.1.30) which has a function to convert glycerol into glycerol-3-phosphate in the presence of ATP and glycerol-3-phosphate oxidase (GPO)(EC.1.1.3) which generate hydrogen peroxide from glycerol-3-phosphate, as well as a system containing glycerol oxidase (GO)(EC. 1.1.3.21) which generates hydrogen peroxide from glycerol as a substrate.

In one embodiment of the present invention, the method for eliminating free glycerol comprises decomposing glycerol with an enzyme system, which generates hydrogen peroxide from free glycerol, to yield hydrogen peroxide, and then eliminating said hydrogen peroxide generated.

After removal of glycerol by such a method, TG of a particular lipoprotein can be quantitated as follows. The resulting sample is allowed to react, in the presence of a reagent that inhibits the reaction of lipoproteins other than the particular lipoprotein, with LPL and an enzyme system which generates hydrogen peroxide from glycerol generated in this reaction, and quantitating the generated hydrogen peroxide.

The reagent that inhibits the reaction of lipoproteins other than the particular one includes surfactants which inhibit the reaction of lipoproteins other than the particular one and/or aggregating agent or the like for lipoproteins other than the particular one.

In order to facilitate generation of glycerol from TG of a particular lipoprotein by LPL, it is also possible to use a surfactant and/or an enzyme which allows the reaction of a particular lipoprotein, in the course of quantitation after elimination of free glycerol.

In another embodiment of the present invention, in eliminating free glycerol, it is also possible to choose a method for eliminating free glycerol, which method comprises converting TGs in lipoproteins other than particular one into free glycerol at the same time.

For example, hydrogen peroxide is generated in the presence of a reagent which allows the reaction of lipoproteins other than the particular one using LPL and an enzyme system which generates hydrogen peroxide from free glycerol, and then the resulting hydrogen peroxide is eliminated. Thus, all of TGs other than TG of a particular lipoprotein can be eliminated.

After the elimination reaction, the sample is allowed to react with LPL and an enzyme system which generates hydrogen peroxide from glycerol, and the generated hydrogen peroxide is quantitated. Thus, TG contained in a particular lipoprotein can be quantitated.

The reagent allowing the reaction of lipoproteins other than the particular one includes surfactants which inhibit the reaction of lipoproteins other than the particular one and/or aggregating agents for the particular lipoprotein.

In order to facilitate generation of glycerol from TG of a particular lipoprotein by LPL, it is also possible to add a surfactant and/or an enzyme which allows the reaction of a particular lipoprotein after elimination of free glycerol and TG of lipoproteins other than the particular one.

According to the present invention, the following reagents are provided: reagents for quantitating TG in a particular lipoprotein containing a reagent for inhibiting the reaction of lipoproteins other than the particular one or a reagent for allowing the reaction of lipoproteins other than the particular one, LPL, GK, GPO and peroxidase; or reagents for quantitating TG in a particular lipoprotein containing a reagent for inhibiting the reaction of lipoproteins other than the particular one or a reagent for allowing the reaction of lipoproteins other than the particular one, LPL, GO and peroxidase. In addition to a reagent for allowing there action of lipoproteins other than the particular one, it is possible to add a surfactant and/or an enzyme which allows the reaction of the particular lipoprotein.

In addition, according to the present invention, the following reagents are provided: reagents for quantitating TG in a particular lipoprotein containing a reagent for inhibiting the reaction of lipoproteins other than the particular one or reagent for allowing the reaction of lipoproteins other than the particular one in the final reaction mixture, LPL, GK, GPO and peroxidase; or reagents for quantitating TG in a particular lipoprotein containing a reagent for inhibiting the reaction of lipoproteins other than the particular one or a reagent for allowing the reaction of lipoproteins other than the particular one in the final reaction mixture, LPL, GO and peroxidase.

The above-mentioned respective reagents for quantitative analysis include a form of kit in which the reagents are divided into two or more parts depending on their component.

The phrase "inhibiting the reaction of lipoproteins other than the particular one" means that an enzyme reaction, which includes decomposition of TGs of lipoproteins other than the particular one into glycerol by LPL, is inhibited directly or indirectly, so that TG of the particular lipoprotein is selectively placed in a condition allowing a selective enzyme reaction. The phrase "allowing the reaction of a particular lipoprotein" means that the reaction decomposing TG as substrate in a particular lipoprotein by LPL into glycerol is allowed by direct or indirect action to the particular lipoprotein.

The method of measurement of the present invention is specifically described as follows.

When a particular lipoprotein is HDL:

In measurement of TG in HDL, it is preferable to add a reagent for inhibiting the reaction of lipoproteins other than HDL, such as an aggregating agent for lipoproteins other than HDL which prevents decomposition of TG in LDL and VLDL by LPL, a surfactant for inhibiting the reaction of lipoproteins other than HDL, and the like, in order to prevent occurrence of errors in the results of measurement of TG content in HDL, which errors are caused by coexistence of TGs In lipoproteins (specifically, LDL and VLDL) other than HDL.

For example, addition of a sample, GK and GPO or GO to an aqueous solution containing a buffer agent generates hydrogen peroxide from free glycerol in the sample. Then, an enzyme, e.g., catalase, which eliminates the hydrogen peroxide generated, or one of coupling-type chromogens and peroxidase are added to the reaction mixture concurrently, and allowed to react at 10 to 50° C., preferably 25 to 40° C., for 3 to 10 minutes, preferably 4 to 5 minutes.

In this reaction, the free glycerol contained in the sample is completely eliminated.

Subsequently, LPL, or LPL and a surfactant for inhibiting the reaction of lipoproteins other than HDL are added to the reaction mixture to generate glycerol from TG in HDL. Thus, hydrogen peroxide is generated from the resulting glycerol with GK and GPO or GO in the reaction mixture. In this situation, when one of coupling-type chromogens and peroxidase have been added in advance, the other chromogen is added to the reaction mixture, or alternatively when catalase has been added, a coupling-type chromogen and peroxidase are added. Then, the mixture is allowed to react at 10 to 50° C., preferably 25 to 40° C., for 2 minutes or longer, preferably 3 to 10 minutes.

Thus, the quantitation of TG in HDL can be achieved by quantitating the pigment produced in the above-mentioned reaction.

In this connection, it is possible to add the reagent for inhibiting the reaction of lipoproteins other than HDL at the time of elimination reaction of free glycerol. If necessary, it is also possible to add to a buffer a co-factor required for an enzyme reaction, e.g., ATP for GK reaction, or an agent for eliminating inhibitors in sera, e.g., ascorbate oxidase.

As for aggregating agents for lipoproteins other than HDL, combination of a polyanion and a bivalent metal salt, antibody aggregating lipoproteins other than HDL, polyoxyethylene glycol (PEG), and the like, are exemplified. The polyanion includes heparin or salts thereof, phosphotungstic acid or salts thereof, dextransulfate or salts thereof, sulfated cyclodextrin or salts thereof, sulfated oligosaccharide or salts thereof, and the like; the cyclodextrin includes α-cyclodextrin, β-cyclodextrin, γ-cyclodextrin, etc.; the oligosaccharide includes maltotriose, maltotetrose, maltopentose, maltohexose, maltoheptose, etc.; the salt includes sodium salts, potassium salts, lithium salts, ammonium salts, magnesium salts, etc. The bivalent metal salt includes magnesium salts, calcium salts, manganese salts, nickel salts, cobalt salts, and the like, and the magnesium salts are particularly preferred.

The polyanion may preferably be used in an amount of 0.1 g/L to 50 g/L. For example, 0.02 to 10 mM heparin of molecular weight 5000 to 20000 or salts thereof, 0.1 to 10 mM phospho-tungstic acid of molecular weight 4000 to 8000 or salts thereof, 0.01 to 5 mM dextransulfate of molecular weight 10000 to 500000 or salts thereof, 0.1 to 20 mM dextransulfate of molecular weight 1000 to 10000 or salts thereof, 0.1 to 50 mM sulfated cyclodextrin of molecular weight 1000 to 3000 or salts thereof, 0.1 to 50 mM sulfated oligosaccharide of molecular weight 400 to 3000 or salts thereof, or their mixture, and the like are preferably used. More preferably, 0.03 to 1 mM heparin of molecular weight 14000 to 16000 or salts thereof, 0.1 to 3 mM phosphotungstic acid of molecular weight 5000 to 7000 or salts thereof, 0.01 to 5 mM dextransulfate of molecular weight 150000 to 250000 or salts thereof, 0.1 to 10 mM dextransulfate of molecular weight 1000 to 5000 or salts thereof, 0.1 to 10 mM sulfated cyclodextrin of molecular weight 1000 to 2000 or salts thereof, 0.1 to 10 mM sulfated oligosaccharide of molecular weight 400 to 2000 or salts thereof, or their mixture, and the like are used.

As for the bivalent metal salt, 0.1 to 50 mM magnesium salts, calcium salts, manganese salts, nickel salts, cobalt salts, and the like may be used, and preferably, 0.1 to 50 mM magnesium salts are used.

As for the antibody aggregating lipoproteins other than HDL, anti-apo-B antibody, anti-apo-C antibody, and the like are exemplified. The anti-apo-B antibody or the anti-apo-C antibody includes IgG fractions of anti-apo-B antiserum or anti-apo-C antiserum, respectively, which are prepared by immunizing rabbits with apoprotein B or apoprotein C purified from human serum, then applying the resulting anti-apo-B antiserum or anti-apo-C antiserum to ammonium sulfate precipitation, followed by salting-out, or alternatively they may be anit-apo-B monoclonal antibody or anti-apo-C monoclonal antibody prepared by immunizing mice with said apoprotein B or said apoprotein C (Monoclonal Antibody; Introduction of Experimental Procedure, Tamie Ando, Kodansha Scientific, page 21, 1991).

As PEG, 0.3 to 100 mM PEG of molecular weight 4000 to 25000 is preferably used, and more preferably 1.0 to 50 mM PEG of molecular weight 5000 to 22000 is used.

As for the surfactant which inhibits the reaction of lipoproteins other than HDL, polyoxyethylene glycol alkyl ether, polyoxyethylene glycol alkyl phenyl ether, polyoxyethylene glycol-polyoxypropylene glycol condensate [Pluronic F-68, Pluronic F-88 (Asahi Denka Kogyo KK), etc.], polyoxyethylene glycol alkyl ether sulfate, surfactants such as alkylbenzenesulfonate disclosed in Japanese Laid-Open Patent Application No. 8-201393, surfactants referred to as low foaming wetting penetrants including polyoxyethylene glycol derivatives such as Emulgen 220, Emulgen 913, Emul 20C, Emulgen B-66, etc., anionic surfactants such as dodecylbenzene-sulfonates, etc., and surfactants of bile acid type such as cholic acid, deoxycholic acid, etc., are exemplified. Preferably, Pluronic F-68, Pluronic F-88 (Asahi Denka Kogyo KK), etc., Emulgen 220, Emulgen 913, Emul 20C, Emulgen B-66, dodecylbenzenesulfonates, and the like are exemplified. The concentration of the surfactant is preferably in a range of 0.01 to 5%.

(2) When the particular lipoprotein is LDL:

In a measurement method of TG in LDL, TGs in lipoproteins other than LDL (specifically, HDL and VLDL) are converted into free glycerol, which is then eliminated completely together with free glycerol in the sample. Thus, TG in LDL can be quantitated specifically. In carrying out the quantitation of TG in LDL, TGs in lipoproteins other than LDL are allowed to react with LPL in the presence of a reagent allowing the reaction of lipoproteins other than LDL, for example, polyoxyethylene glycol alkyl phenyl ether [HLB (index of hydrophile-lipophile balance in the structure of surfactant) is 15 or higher], surfactant which allows the reaction of lipoproteins other than LDL, e.g., surfactant referred to as low foaming wetting penetrant including polyoxyethylene glycol derivatives, or a surfactant combined with an LDL-aggregating agent [polyanion (sometimes including bivalent metal salt), antibody aggregating LDL or the like], and the like, to be converted into free glycerol. This is preferably carried out as follows.

To an aqueous solution containing a buffer is added a sample, a reagent allowing the reaction of lipoproteins other than LDL, LPL, a combination of GK and GPO or GO. TGs in lipoproteins other than LDL in the sample are decomposed by LPL to yield free glycerol, which is further decomposed together with free glycerol originally present in the sample with an enzyme system of GK and GPO or GO to yield hydrogen peroxide. In order to eliminate the resulting hydrogen peroxide, the above-mentioned catalase or one of coupling-type chromogens and peroxidase are added to the buffer concurrently with the above-mentioned LPL, and the mixture is allowed to react at 10 to 50° C., preferably 25 to 40° C., for 3 to 10 minutes, preferably 4 to 5 minutes.

In this reaction, TGs except one in LDL are completely eliminated.

Subsequently, a surfactant allowing the reaction of LDL and the other coupling-type chromogen or said surfactant and LPL are added to the reaction mixture. Thus, TG in LDL is decomposed to yield glycerol, which is further decomposed with an enzyme system of GK and GPO or GO contained in the reaction mixture to generate hydrogen peroxide. In order to quantitate the generated hydrogen peroxide, when one of coupling-type chromogens and peroxidase have been added in advance, the other chromogen is added to the reaction mixture, or alternatively when catalase has been added, a coupling-type chromogen and peroxidase are added. Then, the mixture is allowed to react at 10 to 50° C., preferably 25 to 40° C. for 2 minutes or longer, preferably 3 to 10 minutes.

According to the above-mentioned method, TG in LDL can be quantitated specifically.

In order to facilitate practice of the enzyme reaction, a co-factor such as ATP required for the reaction of GK may be added to the buffer.

The surfactant used in elimination of TGs in lipoproteins other than LDL, which allows the reaction of lipoproteins other than LDL, includes those as described in the example of the above-mentioned quantitation of HDL, as well as other agents of relatively high HLB such as Emulgen A-60 or the like. Specifically, in addition to the above-mentioned surfactants, polyoxyethylene glycol alkyl phenyl ether such as Nonion NS-220, NS-230, NS-240, HS-220, HS-240, etc., are exemplified. These are emulsifying agents for rubber or plastics, and most of them have HLB of 15 or higher. These may be used as a mixture. In general, HLB has additivity and it is common knowledge that the high HLB agent can be used in combination with the lower HLB one to properly adjust an HLB value. The concentration of the surfactant is preferably in a range of 0.01 to 5%.

As for the polyanions, bivalent metal salts, and antibodies aggregating LDL used in elimination of TGs in lipoproteins other than LDL, the polyanions, bivalent metal salts, and antibodies aggregating lipoproteins other than LDL as described in the example of the above-mentioned HDL quantitation and the like are exemplified.

As the surfactant which allows the reaction of LDL, non-ionic surfactants in which LDL is soluble, for example, Emulgen 709, Triton X-100, Triton DF-16, Triton LO-5, etc. are used alone or in combination. Specifically, a surfactant having high solubilizing ability, such as Triton DF-16 (Sigma), Emulgen 709 (Kao Corporation), etc. are exemplified. The concentration of the surfactant is preferably in a range of 0.01 to 5%.

As for the enzyme, usually commercially available LPL, GK, GPO, GO, peroxidase, and the like are exemplified. In order to further enhance specificity and stability of these enzymes, enzymes chemically modified with a group containing polyoxyethylene glycol as a major part, a group containing polypropylene glycol as a major part, a group containing a sugar moiety in its structure such as water-soluble oligosaccharide residue, sulfopropyl group, polyurethane group, and the like, are used. Alternatively, an enzyme which is made by taking out the gene of said enzyme by genetic manipulation and introducing it into another microorganism for expression or a chemically modified derivative thereof, or an enzyme which is made by applying said gene to modification and expression or a chemically modified derivative thereof, or the like may preferably be used.

The reagents for modifying the enzyme (chemical modifiers) are exemplified by: a compound in which polyoxyethylene glycol is bound to a group to which an amino group can be bound [e.g., Sunbright VFM4101 (made by NOF Corporation) in which polyoxyethylene glycol is bound to a group to which an amino group can be bound, e.g. N-hydroxysuccinimido group]; Sunbright AKM series, ADM series, and ACM series [these are made by NOF Corporation; Journal of Chemical Engineering of Japan, Vol. 20, No. 3, 459 (1994)] having a polyoxyalkylene glycol structure and an acid anhydride structure; a compound comprises polyoxyethylene glycol and polyoxypropylene glycol which is bound to a group to which an amino group can be bound; a copolymer of polyoxyethylene glycol monomethacryl monomethyl ether and maleic anhydride; and the like. In addition, a chemical modifier for polyurethane, i.e., Polyurethane P4000 activated (made by Boehringer Mannheim GmbH; Explanatory leaflet for Enzyme modification set), a chemical modifier for dextran, i.e., Dextran T40, TCT-activated (the same as above), 1,3-propanesultone, and the like may be used. Using these chemical modifiers, the enzymes may be modified with a group containing polyoxyethylene glycol as a major part, a group containing polyoxypropylene glycol as a major part, a group containing a copolymer of polyoxypropylene glycol and polyoxyethylene glycol, a group containing a sugar moiety in its structure, a sulfopropyl group, a polyurethane group, and the like.

The following is an example of a method for reacting an enzyme with the above-mentioned chemical modifiers, but the present invention is not limited thereto. First, an enzyme is dissolved in a buffer of pH 8 or higher such as HEPES buffer, to which, for example, 0.01 to 500 equimolar amount of Sunbright is added at 0 to 50° C., and the mixture is stirred for 5 to 60 minutes. This reaction mixture is used directly, or, if required, after removal of low molecular materials through an ultrafiltration membrane.

The necessary amount of the enzyme used in the present invention is, preferably, 0.1 to 20 unit (U)/ml for LPL, 0.2 to 30 U/ml for GK, 1 to 50 U/ml for GPO, 1 to 100 U/ml for peroxidase, and 2 to 200 U/ml for GO. The amount of ATP necessary for use of GK is 0.05 mg/ml to 5 mg/ml.

The chromogen preferably used in detection of hydrogen peroxide includes a combination of 4-aminoantipyrine with a phenol such as phenol, 4-chlorophenol, m-cresol, 3-hydroxy-2,4,6-triiodobenzoic acid (HTIB), etc.; a combination (coupling-type chromogen) of 4-aminoantipyrine with an aniline known as a Trinder reagent (Dojindo Laboratories, General Catalogue 19th ed., 1994) such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-3-sulfopropyl)-3,5-dimethoxyaniline (HDAOS), N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl)aniline, N-ethyl-N-(2-hydroxy-3-sulfopropyl)-3,5-dimethoxyaniline, etc., or N-ethyl-N-(3-methylphenyl)-N'-succinylethylenediamine (EMSE), N-ethyl-N-(3-methylphenyl)-N'-acetylethylenediamine, N-ethyl-N-sulfopropyl-3,5-dimethoxy-4-fluoroaniline, N-sulfopropyl-3,5-dimethoxy-4-fluoroaniline, N-ethyl-N-(2-hydroxy-3-sulfopropyl)-3,5-dimethoxy-4-fluoroaniline, N-(2-hydroxy-3-sulfopropyl)-3,5-dimethoxy-4-fluoroaniline, and the like. In addition, it is possible to use 10-(N-carboxymethylaminocarbonyl)-3,7-bis (dimethylamino)phenothiazine (MCDP), bis[3-bis(4-chlorophenyl)methyl-4-dimethylaminophenyl]amine (BCMA), or the like. The concentration of these chromogens is preferably in a range of 0.02 to 2 g/L.

In the present invention, a buffer agent with which a solution can have buffering action can be used. The preferred buffer agent includes phosphates, borates, organic acid salts, and Good's and Tris buffer agents. The concentration of the buffer is preferably 10 to 200 mM. Preferred pH range is 5 to 9.

BEST MODE FOR CARRYING OUT THE INVENTION

The followings are working examples.

EXAMPLE 1

| Measurement of TG in LDL | | |
|---|---|---|
| Reagent 1 (pH 6.25) | Buffer [Piperazine-1,4-bis(2-ethanesulfonic acid)(PIPES)] | 50 mM |
| | TOOS (Dojindo Laboratories) | 0.3 g/L |
| | ATP 2Na salt (Wako Pure Chemical Industries, Ltd.) | 2.5 g/L |
| | Ascorbic acid oxidase (Asahi Kasei Corporation) | 3 kU/L |
| | GK (Toyobo Co., Ltd.) | 1 kU/L |
| | GPO (Asahi Kasei Corporation) | 8 kU/L |
| | Peroxidase (Toyobo Co., Ltd.) | 20 kU/L |
| | PEG modified LPL (Toyobo Co., Ltd.) | 1.5 kU/L |
| | LPL III (Amano) | 60 kU/L |
| | Nonion NS-230 (NOF Corporation) | 0.1% |
| | Magnesium sulfate heptahydrate (Wako Pure Chemical Industries, Ltd.) | 0.5 g/L |
| Reagent 2 (pH 6.25) | Buffer (PIPES) | 50 mM |
| | Emulgen 709 | 0.6% |
| | Triton DF-16 | 0.3% |
| | 4-Aminoantipyrine (Wako Pure Chemical Industries, Ltd.) | 0.5 g/L |

Figure 1:
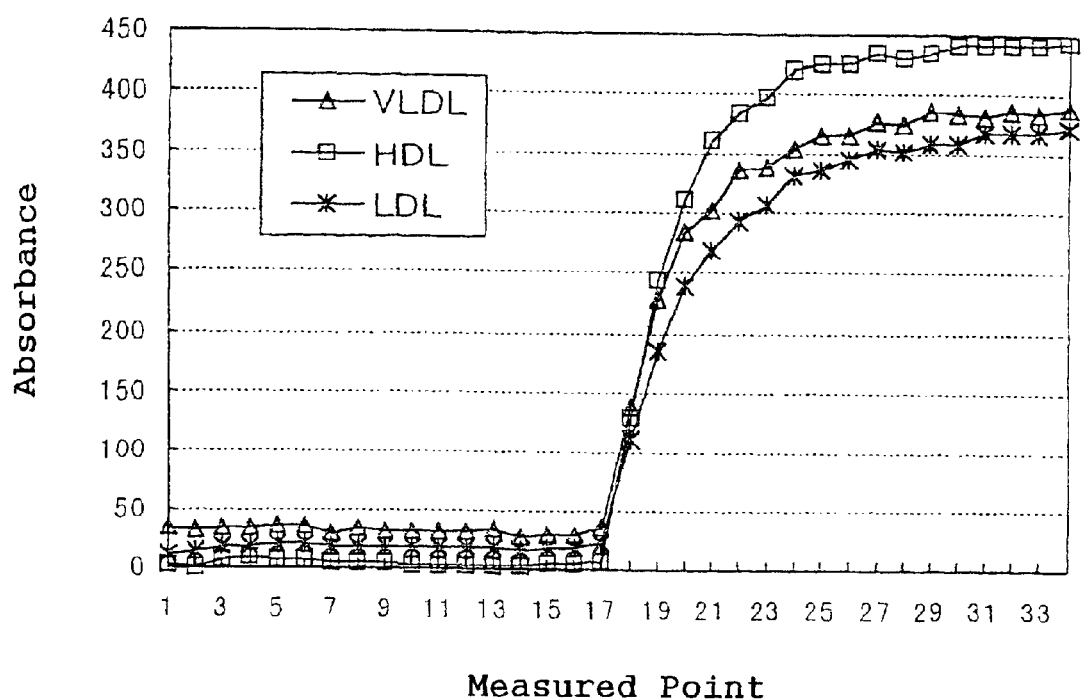
FIG. 1 shows the absorbance versus time measured with a reagent for measuring total TG for HDL, LDL and VLDL fractions.
Figure 2:
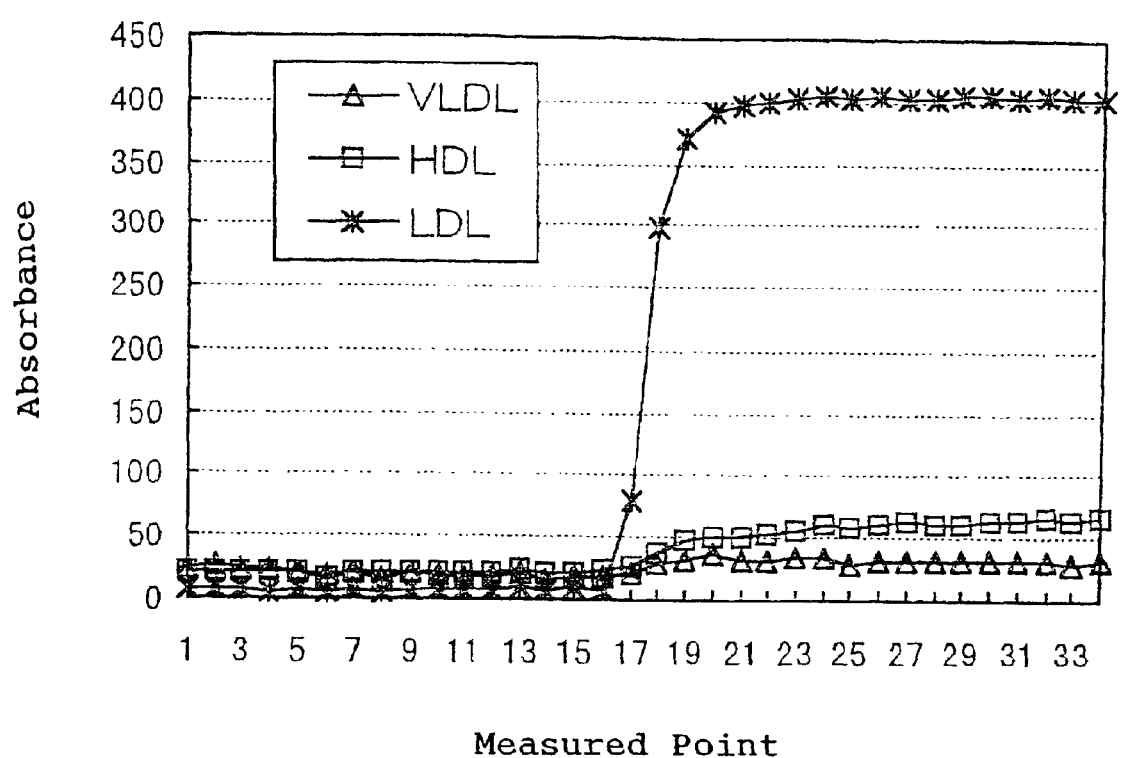
FIG. 2 shows the absorbance versus time for HDL, LDL and VLDL fractions measured by the method in Example 1.

The specificity was confirmed by tracing the time course under the condition of the following parameters using a Hitachi Auto-Analyzer 7170. As a sample, HDL, LDL and VLDL fractions fractionated from human serum by ultracentrifugation were used. FIG. 1 shows the time course measured with a reagent for measuring total TGs (Kyowa Medex Co., Ltd.) for TG contained in each lipoprotein, and FIG. 2 shows the time course measured with the above-mentioned reagents. In treatment with the reagent for measuring total TG, all of TGs contained in each lipoprotein are involved in the reaction. On the other hand, in treatment with the above-mentioned reagents, free glycerol and TGs in HDL and VLDL in the sample react first in the first reaction to generate hydrogen peroxide, which is eliminated by catalase at the same time. At the time when the reagent 2 is added, the reaction occurs only in LDL. Thus, a system for specifically quantitating TG in LDL was established. In addition, serum samples of healthy subjects were directly analyzed as samples without fractionation using the same Hitachi 7170 machine into which the following parameters were input. As standard solutions, the above-mentioned LDL fractions were used, of which the values were measured with a Determiner L TG (made by Kyowa Medex Co.) and input as parameters into the analyzer.

Thus resulting analytical values were compared with those obtained by the following method as a comparative one. The correlation coefficient was 0.918.

Comparative Method

According to the standard method for measuring HDL provided by US CDC, each sample was ultracentrifuged, and total TGs were quantitated for the resulting HDL and LDL fractions (TG(L+H)). The specified fractionating agent (heparin-manganese) was added thereto, and the difference of TG(H) value for the precipitated and separated HDL, [TG(L+H)−TG(H)], was used.

Parameters

Analytical method: 2 point end
Photometric point: 16–34, range; 10 minutes
Measuring wavelength: 546 nm; Side wavelength: 700 nm
Sample volume: 3.2 µl
Reagent volume: R1: 240 µl; R2: 80 µl

EXAMPLE 2

| Measurement of TG in HDL | | |
| --- | --- | --- |
| Reagent 1 (pH 6.25) | Buffer (PIPES) | 50 mM |
| | TOOS (Dojindo Laboratories) | 0.3 g/L |
| | ATP 2Na salt (Wako Pure Chemical Industries, Ltd.) | 2.5 g/L |
| | Ascorbic acid oxidase (Asahi Kasei Corporation) | 3 kU/L |
| | GK (Toyobo Co., Ltd.) | 1 kU/L |
| | GPO (Asahi Kasei Corporation) | 8 kU/L |
| | Catalase (Sigma) | 300 kU/L |
| | Sodium dextransulfate | 0.2 g/L |
| | Magnesium sulfate heptahydrate (Wako Pure Chemical Industries, Ltd.) | 0.5 g/L |
| Reagent 2 (pH 6.25) | Buffer (PIPES) | 50 mM |
| | Emulgen B-66 (Kao Corporation) | 20 g/L |
| | Calcium chloride dihydrate | 0.1 g/L |
| | 4-Aminoantipyrine (Wako Pure Chemical Industries, Ltd.) | 0.5 g/L |
| | Sodium azide | 0.5 g/L |
| | LPL (Asahi Kasei Corporation) | 1000 kU/L |
| | Peroxidase (Toyobo Co., Ltd.) | 20 kU/L |

Figure 3:
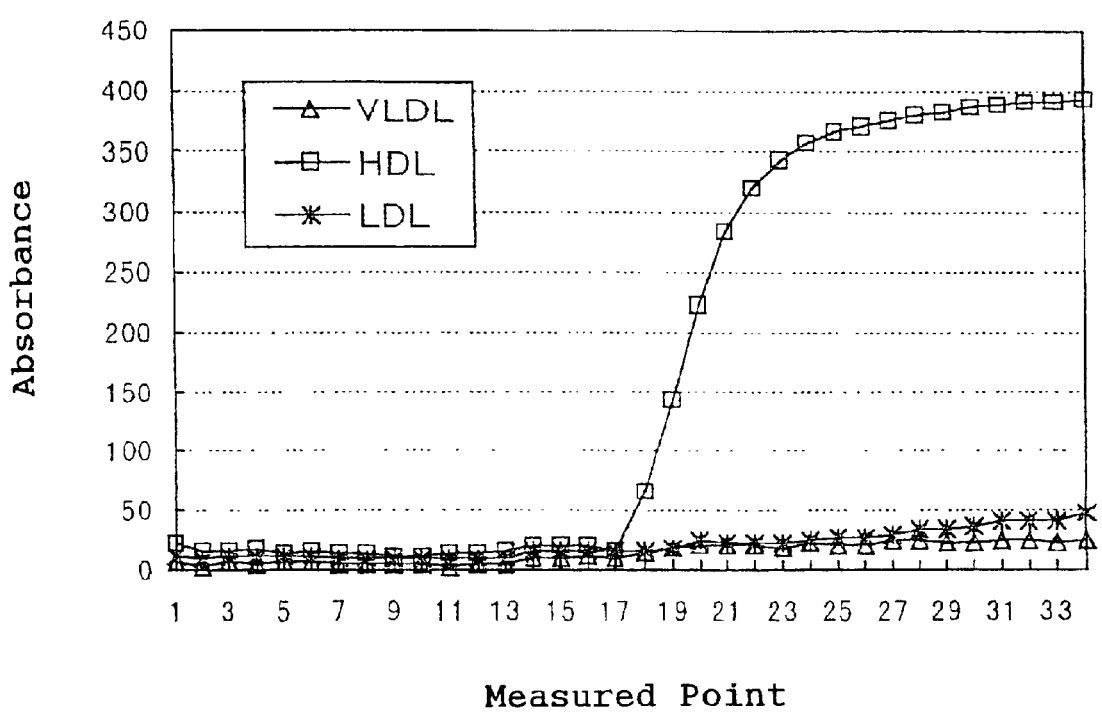
FIG. 3 shows the absorbance versus time for HDL, LDL and VLDL fractions measured by the method in Example 2.

The specificity was confirmed by tracing the time course under the condition of the following parameters using a Hitachi Auto-Analyzer 7170. As a sample, the same HDL, LDL and VLDL fractions fractionated from human serum by ultracentri-fugation as Example 1 were used. As shown in FIG. 3, in treatment with the reagent 1 in the first reaction, free glycerol reacts first to generate hydrogen peroxide, which is eliminated by catalase at the same time. At the time when the reagent 2 is added, the reaction occurs only in HDL. Thus, a system for specifically quantitating TG in HDL was established. In addition, serum samples of healthy subjects were directly analyzed as samples without fractionation using the same Hitachi 7170 machine. As standard solutions, the above-mentioned HDL fractions were used, of which the values were measured with a Determiner L TG (made by Kyowa Medex Co., Ltd.) and input as parameters into the analyzer.

Thus resulting analytical values were compared with those obtained by the following method as a comparative one. The correlation coefficient was 0.911.

Comparative Method

According to the standard method for measuring HDL provided by US CDC, each sample was ultracentrifuged. The specified fractionating agent (heparin-manganese) was added to the resulting HDL and LDL fractions, and the TG value of the HDL portion in the supernatant obtained by precipitation and separation was used.

Parameters

Analytical method: 2 point end
Photometric point: 16–34, range; 10 minutes
Measuring wavelength: 546 nm; Side wavelength: 700 nm
Sample volume: 3.2 µl
Reagent volume: R1: 240 µl; R2: 80 µl Industrial Applicability According to the present invention, a method for conveniently quantitating TGs contained in various lipoproteins is provided. Particularly, quantitation of TG in LDL affords an index of the yield of small dense LDL, which may relate to prevention of arteriosclerosis.

What is claimed is:

1. A method for quantitating triglyceride in a particular lipoprotein in a sample containing triglycerides in a mixture of lipoproteins and free glycerol which comprises the steps of:

(1) eliminating the free glycerol from the sample,
   (2) reacting the sample from step (1) which contains the mixture of the lipoprotein with lipoprotein lipase to produce glycerol in the presence of a reagent which inhibits a reaction of lipoproteins with the lipoprotein lipase other than the particular lipoprotein,
   (3) reacting the sample from step (2) with an enzyme system which generates hydrogen peroxide from free glycerol, and
   (4) quantitating generated hydrogen peroxide from step (3),
   wherein the particular lipoprotein is high density lipoprotein.

2. The method according to claim 1, wherein the reagent in step (2) comprises a surfactant which inhibits the reaction of lipoproteins other than the particular one or an aggregating agent for lipoproteins other than the particular one.

3. The method according to claim 2, wherein the surfactant is selected from the group consisting of polyoxyethylene glycol alkyl ether, polyoxyethylene glycol alkyl phenyl ether, polyoxyethylene glycol-polyoxypropylene glycol condensate, polyoxyethylene glycol alkyl ether sulfate, polyoxyethylene glycol derivative which is a low foaming wetting penetrant, anionic surfactant and bile acid.

4. The method according to claim 2, wherein the aggregating agent is selected from the group consisting of a combination of a polyanion and a bivalent metal salt, an antibody aggregating lipoproteins other that the particular lipoprotein and polyoxyethylene glycol.

5. The method according to claim 1, wherein the reagent in step (2) comprises a polyoxyethylene glycol derivative which is a low foaming wetting penetrant.

6. The method according to claim 1, wherein the reagent in step (2) comprises a combination of polyanion and bivalent metal salt.

7. The method according to claim 1, wherein step (1) comprises (A) utilizing an enzyme system to produce hydrogen peroxide from free glycerol, and (B) then eliminating hydrogen peroxide so generated.

8. The method according to claim 7, wherein step (B) comprises utilizing one of coupling-type chromogens and peroxidase.

9. The method according to claim 1, wherein step (4) comprises allowing hydrogen peroxide to react with peroxidase and a chromogen to yield a pigment, and quantitating the pigment as absorbance.

10. The method according to claim 9, wherein the chromogen comprises 4-aminoantipyrine and Trinder reagent.

11. The method according to any one of claims 1 to 10, wherein in step (3) the enzyme system that generates hydrogen peroxide from free glycerol comprises glycerol kinase and glycerol 3-phosphate oxidase.

12. The method according to any one of claims 1 to 10, wherein in step (3) the enzyme system that generates hydrogen peroxide from free glycerol comprises glycerol oxidase.

13. A method for quantitating triglyceride in a particular lipoprotein which comprises the steps of:
   (1) eliminating the free glycerol and triglycerides in lipoproteins other than the particular one from a sample, said sample containing triglycerides in a mixture of lipoproteins and free glycerol, in the presence of a reagent that allows the reaction of lipoprotein other than the particular one,
   (2) reacting the sample from step (1) with lipoprotein lipase to produce glycerol in the presence of a surfactant or enzyme that allows the reaction of a particular lipoprotein with the lipoprotein lipase,
   (3) reacting the sample from step (2) with an enzyme system which generates hydrogen peroxide form free glycerol, and
   (4) quantitating generated hydrogen peroxide from step (3),
   wherein the particular lipoprotein is low density lipoprotein.

14. The method according to claim 13, wherein the reagent in step (1) comprises a surfactant that allows the reaction of lipoproteins other that the particular one.

15. The method according to claim 14, wherein the reagent in step (1) comprises polyoxyethylene glycol alkyl phenyl ether (having an HLB of 15 or higher) or polyoxyethylene glycol derivatives which are a low foaming wetting penetrant.

16. The method according to claim 13, wherein the reagent in step 1 comprises a surfactant that allows the reaction of lipoproteins other than the particular one and an aggregating agent for the particular lipoprotein.

17. The method according to claim 16, wherein the aggregating agent comprises polyanion or antibody aggregating the particular lipoprotein.

18. The method according to claim 13, wherein the surfactant comprises a non-ionic surfactant in which the particular lipoprotein is soluble.

19. The method according to claim 13, wherein step (1) comprises (A) utilizing an enzyme system to produce hydrogen peroxide from free glycerol, and (B) then eliminating hydrogen peroxide so generated.

20. The method according to claim 19, wherein step (B) comprises utilizing one of coupling-type chromogens and peroxidase.

21. The method according to claim 13, wherein step (4) comprises allowing hydrogen peroxide to react with peroxidase and a chromogen to yield a pigment, and quantitating the pigment as absorbance.

22. The method according to claim 21, wherein the chromogen comprises 4-aminoantipyrine and Trinder reagent.

23. The method according to any one of claims 13 to 22, wherein in step (3) enzyme system that generates hydrogen peroxide from free glycerol comprises glycerol kinase and glycerol 3-phosphate oxidase.

24. The method according to any one of claims 13 to 22, wherein in step (3) the enzyme system that generates hydrogen peroxide from free glycerol comprises glycerol oxidase.

* * * * *

ㅤ
UNITED STATES PATENT AND TRADEMARK OFFICE
CERTIFICATE OF CORRECTION

PATENT NO.    : 6,811,994 B1
DATED         : November 2, 2004
INVENTOR(S)   : Kazuhito Miyauchi et al.

It is certified that error appears in the above-identified patent and that said Letters Patent is hereby corrected as shown below:

Title page,
Item [56], References Cited, OTHER PUBLICATIONS, "Apoliprotein E" should read -- Apolipoprotein E --; and
FOREIGN PATENT DOCUMENTS, "9121895" should read -- 9-121895 --; and "JP 58-47499 3/1958" should read -- JP 58-47499 3/1983 --.
Item [57], ABSTRACT,
Line 3, "trigyceride" should read -- triglyceride --.

Column 1,
Line 63, "have" should read -- has --; and
Line 65, "have" should read -- having --.

Column 2,
Line 11, "LPL" should read -- ¶ LPL --.

Column 3,
Line 15, "there action" should read -- the reaction --.

Column 7,
Line 17, "propanesultone," should read -- propanesulfone, --.

Column 8,
Line 24, "followings" should read -- following --.

Column 9,
Line 59, "ultracentri-fugation" should read -- ultracentrifugation --.

Column 10,
Line 63, "lipoproteins" should read -- lipoprotein --.

Column 11,
Line 37, "form" should read -- from --.

UNITED STATES PATENT AND TRADEMARK OFFICE
CERTIFICATE OF CORRECTION

PATENT NO.   : 6,811,994 B1
DATED        : November 2, 2004
INVENTOR(S)  : Kazuhito Miyauchi et al.

It is certified that error appears in the above-identified patent and that said Letters Patent is hereby corrected as shown below:

Column 12,
Line 3, "that" should read -- than --.

Signed and Sealed this

Fifth Day of April, 2005

JON W. DUDAS
*Director of the United States Patent and Trademark Office*